United States Patent [19]

Matsumura et al.

[11] 4,331,763
[45] May 25, 1982

[54] PROCESS FOR PRODUCTION OF ASCORBATE OXIDASE

[75] Inventors: Eiji Matsumura; Hidehiko Ishikawa; Hideo Misaki, all of Shizuoka, Japan

[73] Assignee: Toyo Jozo Kabushiki Kaisha, Shizuoka, Japan

[21] Appl. No.: 217,178

[22] Filed: Dec. 16, 1980

[30] Foreign Application Priority Data

Dec. 21, 1979 [JP] Japan .............................. 54-167163

[51] Int. Cl.$^3$ .............................................. C12N 9/04
[52] U.S. Cl. ................................................. 435/190
[58] Field of Search ................................... 435/190, 25

[56] References Cited

U.S. PATENT DOCUMENTS 4,160,696  7/1979  Wu ........................................ 435/25

OTHER PUBLICATIONS

"Enzyme Handbook", vol. 1, p. 229, by Thomas E. Barman; published 1969.
"Enzyme Handbook", pp. 158-159, Editor Shiro Akabari, Publisher K. K. Asakura Publ., 1st ed. Apr. 30, 1966-2nd Dec. 20, 1966.
Makino's New illustrated Flora of Japan", by Tomitaro Makino, Dr. Sc., 1961, pp. 11 and 612.

*Primary Examiner*—Lionel M. Shapiro
*Attorney, Agent, or Firm*—Young & Thompson

[57] ABSTRACT

Ascorbate oxidase is produced by extraction from plants of the genus Sechium, particularly the species thereof which is *Sechium edule* Sw. The crushed plant tissues are extracted with an aqueous alkaline solvent, preferably at about pH 11. The extract is then subjected to centrifugation, concentration under vacuum, salting out with ammonium sulfate and solvent fractionation with acetone, to prepare crude ascorbate oxidase, which is then further purified by dialysis, ion exchange chromatography, adsorption chromatography and gel filtration. The ascorbate oxidase thus obtained has an optimum pH of about 7, a km value of 0.3 mM, an isoelectric point of around pH 6.3 and a molecular weight of about 100,000.

2 Claims, 2 Drawing Figures

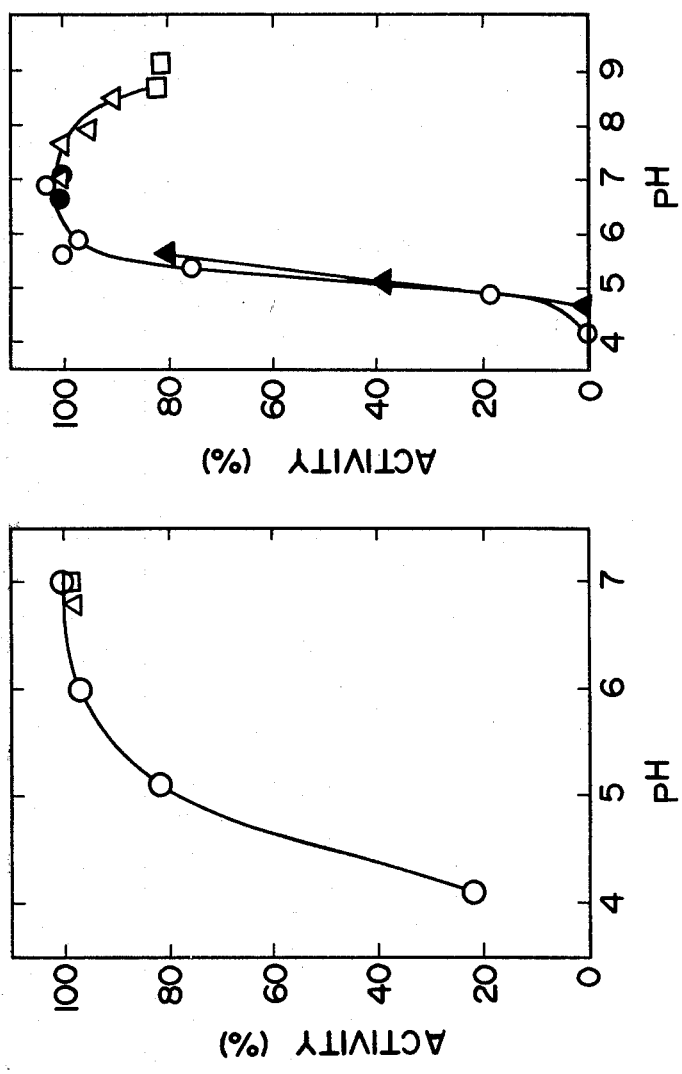

PROCESS FOR PRODUCTION OF ASCORBATE OXIDASE

The present invention relates to a process for the production of ascorbate oxidase, and ascorbate oxidates thus produced.

Ascorbate oxidase catalyzes a reaction which produces one mole of dehydroascorbic acid and one mole of water from one mole of ascorbic acid and ½ mole of oxygen, and falls in the enzyme classification EC 1. 10. 3. 3. L-Ascorbate: oxygen oxidoreductase; common name: ascorbate oxidase. Such enzymes have been prepared from pericarps of genus Cucurbita and genus Cucumis and have been reported to exist in several seedlings [Enzyme Handbook, pages 158–159, 1966, Asakura Publ. Co.]. Ascorbate oxidase of genus Cucurbita and genus Cucumis has a molecular weight of about 140,000 and exists mainly in pericarps of the said plants. The sarcocarp thereof has only a trace of activity, and so the preparation of ascorbate oxidase has been only from the separated pericarps, with the result that the yield was quite low.

Ascorbate oxidase in seedlings has been detected by observing an oxidative action of seedlings extract on ascorbic acid. However, substantial and discrete enzyme isolation and the preparation of ascorbate oxidase have not been confirmed.

We have examined extensively the potential sources of ascorbate oxidase of various origins, such as green peppers (*Capsicum grossum*), oranges (*Citrus sinensis*), sweet potatoes (*Ipomea batatas*), potatoes (*Solanum tuberosum*) and goosefoot (*Chenopodium ambrosioides* var. anthelminticum), and no ascorbate oxidase activity was found.

We have now found that not only the pericarps but also the whole plants of *Sechium edule* Sw. such as carcocarps, stems and leaves showed strong ascorbate oxidase activity and have extracted and purified ascorbate oxidase from tissues of *Sechium edule* Sw. Also we have found that the extraction was effectively performed by using aqueous alkaline medium.

An object of the present invention is accordingly to provide a process for the production of ascorbate oxidase, in which the said enzyme is extracted from tissues of plants belonging to genus Sechium.

An example of a plant belonging to genus Sechium, according to the present invention, is *Sechium edule* Sw. (=*Chayota edulis* Jacq.) [Makino's illustrated book of the Japanese flora, 1961, p. 612, Hokuryukan Publ. Co.]. Ascorbate oxidase is contained in tissues of the entire plant of *Sechium edule* Sw. such as pericarps, sarcocarps, stems and leaves to an activity of at least 10 U (units)/g., usually 30–50 U/g. in tissues of sarcocarps and leaves, and 20–30 U/g. in tissues of stems. These tissues are used alone or in combination.

Examples of extraction of ascorbate oxidase from *Sechium edule* Sw. are as follows:

Water-washed tissues of *Sechium edule* Sw. are shredded to about 1 cm³ in size. The shredded tissues are immersed in aqueous acetone such as 30–50% acqueous acetone for overnight to remove unnecessary components, and homogenized for extraction with an extracting solvent. Alternatively, shredded tissues are homogenized without immersion in aqueous acetone and so are directly extracted with extracting solvent. The extracting solvent is an aqueous medium such as a buffer solution. An aqueous alkaline medium, preferably an alkaline medium of about pH 11, is advantageously used for extraction in order to avoid the precipitation of ascorbate oxidase caused by unnecessary components. Extraction with such an alkaline medium results in advantageous extraction of the enzyme.

The extract is then subjected to centrifugation, concentration in vacuo, salting-out with ammonium sulfate and solvent fractionation with acetone to prepare crude ascorbate oxidase.

Further purification is effected by dialysis, ion exchange chromatography, adsorption chromatography and gel filtration.

In the accompanying drawing:

FIG. 1 is a graph of optimum pH of the ascorbate oxidase of the present invention; and FIG. 2 is a graph of the pH stability thereof.

The biochemical properties of the thus-obtained ascorbate oxidase of the present invention are as follows:

(1) Enzymatic action:

The enzyme catalyzes a reaction which produces one mole of dehydroascorbic acid and one mole of water from one mole of ascorbic acid and ½ mole of oxygen:

L-Ascorbic acid + ½O₂ → Dehydroascorbic acid + H₂O (2) Substrate specificity:

The enzyme has specific activity for ascorbic acid as follows:

| Substrate | Relative activity (%) |
|---|---|
| L-Ascorbic acid | 100 |
| Glycerol | 0 |
| Glucose | 0 |
| Galactose | 0 |
| Maltose | 0 |
| Ethylene glycol | 0 |

(3) Optimum pH:

As shown in FIG. 1, optimum pH is around pH 7. In FIG. 1, o—o: dimethylglutarate-NaOH buffer, △: phosphate buffer, □: Tris-HCl buffer.

(4) Km value: 0.3 mM.

(5) Isoelectric point: around pH 6.3.

(6) Molecular weight: about 100,000 (determined by Sephacryl S-200).

(7) pH stability:

As shown in FIG. 2, stable at pH 5.7–7.5. In FIG. 2, o—o: dimethylglutarate-NaOH buffer, ●—●: phosphate buffer, □—□: glycine-NaOH buffer, ▲—▲: acetate buffer, △—△: Tris-HCl buffer, at 37° C. for 60 min.

(8) Optimum temperature: around 40° C.

(9) Denaturation by pH and temperature:

Rapidly denatured below pH 4.5 and over 50° C.

(10) Effect of metallic ions and EDTA:

| Additives | Concentration (mM) | Relative Activity (%) |
|---|---|---|
| None | — | 100 |
| NaCl | 10 | 88.4 |
| KCl | 10 | 91.9 |
| LiCl | 10 | 84.9 |
| NH₄Cl | 10 | 91.9 |
| MnCl₂ | 10 | 87.2 |
| CaCl₂ | 10 | 86.0 |
| BaCl₂ | 10 | 77.9 |
| CoCl₂ | 10 | — |
| CuCl₂ | 1 × 10⁻² | — |
| ZnCl₂ | 10 | 17.4 |
| MgCl₂ | 10 | 36.0 |
| NaNO₃ | 10 | 12.8 |
| EDTA | 0.1 | 96.5 |

| Additives | Concentration (mM) | Relative Activity (%) |
|---|---|---|
| EDTA | 1 | 98.8 |
| EDTA | 10 | 107 |

(11) Determination of activity:

2 mM ascorbic acid in dimethylglutarate-NaOH buffer (pH 6.5, 1.0 ml) is added to a 2 ml cell. Enzyme (20 μl) is added at 37° C. and the amount of consumed oxygen is measured with a Galvanic dissolved oxygen meter (Ishikawa Mfg. Co.)

A unit (one unit, 1 U) is defined as the amount of enzyme which takes up 0.5μ mole of oxygen per minute at 37° C.

The enzyme ascorbate oxidase of the present invention can be advantageously used for the cancellation of error caused by ascorbic acid in a sample for clinical assay using oxidase, or for the quantitative assay of ascorbic acid.

The following examples illustrate the present invention but are not to be construed as limiting:

EXAMPLE 1

Washed fruit of Sechium edule Sw. (10 kg) was shredded into 1 cm$^3$ pieces and immersed in 50% aqueous acetone overnight. After filtration, the solids were added to 20 mM Tris-HCl buffer (pH 8.5, 10 lit.) and homogenized in a Waring blender (15,000 r.p.m., for 20 minutes), then filtered through gauze. The filtrate was centrifuged at 5000 r.p.m. for 10 minutes to obtain the supernatant (ascorbate oxidase: 256,000 U). The supernatant was concentrated to 1/10 volume at 60° C. under a reduced pressure of 20 mmHg and centrifuged to separate the insolubles. The supernatant was fractionated with ammonium sulfate to obtain the 0.23–0.52 saturated fraction. The precipitate was dissolved in 20 mM Tris-HCl buffer (500 ml, pH 8.5) and centrifuged to separate the insoluble materials. An equal volume of acetone was added to the supernatant. The precipitate was dissolved in 20 mM Tris-HCl buffer (pH 8.5, 400 ml) and the insolubles were removed by centrifugation. The supernatant solution was dialyzed against 20 mM Tris-HCl buffer (pH 8.5) for 12 hours and the dialyzate was charged on a DEAE-cellulose column (4×60 cm), equilibrated with 20 mM Tris-HCl buffer (pH 8.5) which was washed with 20 mM Tris-HCl buffer (pH 8.5, 1.5 lit.) The column was subjected to linear-gradient elution with 0–0.5 M KCl solutions. Ascorbate oxidase was eluted with 0.08–0.12 M KCl concentrations. The active fractions were collected and concentrated with a membrane filter (Amicon Co.) The concentrate was subjected to Sephacryl S-200 column chromatography (5×100 cm) and the eluted active fractions were collected which were lyophilized to obtain a powder of ascorbate oxidase (specific activity 920 U/mg, 36.2 mg, yield: 13%).

EXAMPLE 2

200 Grams each of the shredded sarcocarps, pericarps, stems and leaves (with petioles) of Sechium edule Sw. were added to 20 mM Tris-HCl buffer (200 ml, pH 8.5) and homogenized with a Waring blender (15,000 r.p.m. for 10 minutes). The homogenate was filtered through gauze and the filtrate was assayed for ascorbate oxidase activity.

Ascorbate oxidase activities are shown as follows:

Sarcocarp: 18.7 U/ml.
Pericarp: 19.2 U/ml.
Stem: 14.6 U/ml.
Leaf (with petiole): 13.3 U/ml.

For purposes of comparison, ascorbate oxidase activity was assayed according to the same procedures in Example 2, for the following materials:
Pumpkin:
  sarcocarp:—
  pericarp with sarcocarp: 14.8 U/ml.
Green pepper:
  sarcocarp, pericarp:—
Sweet potato:
  sarcocarp, pericarp:—
Carrot:
  pericarp: 0.43 U/ml.
  sarcocarp: 0.21 U/ml.
Persimmon:
  pericarp:—
  sarcocarp: 0.65 U/ml.
[—: not detectable]

EXAMPLE 3

A mixture (10 kg) of sarcocarps, pericarps, leaves and stems of Sechium edule Sw. was shredded and immersed in 50% aqueous acetone overnight. After the removal of aqueous acetone, the mixture was washed with water. The washed mixture was added to 20 mM sodium carbonate solution (pH 11, 10 lit.) and homogenized with a Waring blender. The homogenized mixture was filtered through gauze and the filtrate was centrifuged at 5000 r.p.m. for 10 minutes. The supernatant was treated by the same procedures as in Example 1 to obtain ascorbate oxidase powder (specific activity: 940 U/mg).

What is claimed is:

1. A process for the production of ascorbate oxidase, comprising contacting plant tissue of the species Sechium edule Sw. with an aqueous alkaline medium as an extracting solvent, and separating ascorbate oxidase from the solvent solution thereof thus produced.

2. A process as claimed in claim 1, in which the pH of said aqueous alkaline medium is about 11.

* * * * *